US008937186B2

(12) United States Patent
Rende et al.

(10) Patent No.: US 8,937,186 B2
(45) Date of Patent: Jan. 20, 2015

(54) ACIDS REMOVAL AND METHANE CONVERSION PROCESS USING A SUPERSONIC FLOW REACTOR

(71) Applicant: UOP LLC, Des Plaines, IL (US)

(72) Inventors: Dean E. Rende, Arlington Heights, IL (US); Jayant K. Gorawara, Buffalo Grove, IL (US); Debarshi Majumder, Forest Park, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/950,830

(22) Filed: Jul. 25, 2013

(65) Prior Publication Data

US 2014/0058118 A1    Feb. 27, 2014

Related U.S. Application Data

(60) Provisional application No. 61/691,355, filed on Aug. 21, 2012.

(51) Int. Cl.
| | |
|---|---|
| *C07C 7/12* | (2006.01) |
| *C07C 2/78* | (2006.01) |
| *C07C 7/13* | (2006.01) |
| *C07C 7/148* | (2006.01) |
| *B01J 12/00* | (2006.01) |
| *B01J 19/10* | (2006.01) |
| *B01J 19/26* | (2006.01) |

(52) U.S. Cl.
CPC ... *C07C 7/12* (2013.01); *C07C 2/78* (2013.01); *C07C 7/13* (2013.01); *C07C 7/14858* (2013.01); *B01J 12/005* (2013.01); *B01J 19/10* (2013.01); *B01J 19/26* (2013.01); *B01J 2219/00123* (2013.01)
USPC ........... 548/543; 585/325; 585/254; 585/322; 585/324; 585/326; 585/310; 422/128; 548/579; 562/545; 568/467; 568/852; 568/855; 564/204

(58) Field of Classification Search
CPC ...................................................... B01J 19/10
USPC .......................................... 585/539; 422/128
See application file for complete search history.

(56) References Cited

U.S. PATENT DOCUMENTS

| | | | |
|---|---|---|---|
| 748,091 A | 12/1903 | Nethery | |
| 2,581,102 A | 1/1952 | Hodges | |
| 2,822,410 A | 2/1958 | Wojcik et al. | |
| 3,565,940 A | 2/1971 | Brown et al. | |
| 3,615,164 A | 10/1971 | Baker et al. | |
| 3,726,964 A * | 4/1973 | Krejci | 423/455 |
| 3,816,975 A | 6/1974 | Collins | |
| 4,009,219 A | 2/1977 | Tamers | |
| 4,094,777 A | 6/1978 | Sugier et al. | |
| 4,136,015 A | 1/1979 | Kamm et al. | |
| 4,181,662 A | 1/1980 | Sweeney | |
| 4,191,636 A | 3/1980 | Fukui et al. | |
| 4,288,641 A | 9/1981 | Codignola et al. | |
| 4,356,124 A | 10/1982 | Pesa et al. | |
| 4,357,228 A * | 11/1982 | Che | 208/57 |
| 4,387,263 A | 6/1983 | Vogt et al. | |
| 4,426,248 A | 1/1984 | Jackson | |
| 4,493,715 A | 1/1985 | Hogan et al. | |
| 4,544,792 A | 10/1985 | Smith et al. | |
| 4,587,373 A | 5/1986 | Hsia | |
| 4,724,272 A * | 2/1988 | Raniere et al. | 585/500 |
| 4,744,221 A | 5/1988 | Knollmueller | |
| 4,892,567 A | 1/1990 | Yan | |
| 4,929,789 A | 5/1990 | Gupta et al. | |
| 5,026,935 A | 6/1991 | Leyshon et al. | |
| 5,095,163 A | 3/1992 | Barger | |
| 5,096,470 A | 3/1992 | Krishnamurthy | |
| 5,126,308 A | 6/1992 | Barger et al. | |
| 5,191,141 A | 3/1993 | Barger et al. | |
| 5,219,530 A | 6/1993 | Hertzberg et al. | |
| 5,227,570 A | 7/1993 | Tan | |
| 5,232,474 A | 8/1993 | Jain | |
| 5,276,257 A | 1/1994 | Diesen | |
| 5,278,344 A | 1/1994 | Gosling et al. | |
| 5,300,216 A | 4/1994 | Hertzberg et al. | |
| 5,419,884 A | 5/1995 | Weekman et al. | |
| 5,446,232 A | 8/1995 | Chen et al. | |

(Continued)

FOREIGN PATENT DOCUMENTS

| | | |
|---|---|---|
| BY | 7932 C1 | 4/2006 |
| CA | 2391441 A1 | 6/2001 |

(Continued)

OTHER PUBLICATIONS

Ren et al. "Olefins from conventional and heavy feedstocks: Energy use in steam cracking and alternative processes" Energy 2006, 31, 425-451.*
Stocki, J. et al. "Oxidizing pyrolysis of methane in a gaseous heating medium. II. Process studies in a laboratory cyclone combuster" Oxidation Communications (1983), 3(3-4), 163-169.*
Abedi, "Economic Analysis of a New Gas to Ethylene Technology", Thesis—Texas A&M University, May 2007.
Anvari, "Enhancement of 2,3-Butanediol Production by Klebsiella oxytoca PTCC 1402", Journal of Biomedicine and Biotechnology, 2011.
Barnard, "The pyrolysis of tert.-butanol", Trans. Faraday Soc., 1959, vol. 55, pp. 947-951.

(Continued)

*Primary Examiner* — Joseph Kosack
*Assistant Examiner* — Amanda L Aguirre

(57) ABSTRACT

Methods and systems are provided for converting methane in a feed stream to acetylene. The method includes removing at least a portion of acids from a hydrocarbon stream. The hydrocarbon stream is introduced into a supersonic reactor and pyrolyzed to convert at least a portion of the methane to acetylene. The reactor effluent stream may be treated to convert acetylene to another hydrocarbon process. The method according to certain aspects includes controlling the level of acids in the hydrocarbon stream by use of adsorbents or basic solutions.

12 Claims, 1 Drawing Sheet

(56) References Cited

U.S. PATENT DOCUMENTS

| | | |
|---|---|---|
| 5,478,950 A | 12/1995 | Bergfeld et al. |
| 5,482,616 A | 1/1996 | Brahma et al. |
| 5,510,565 A | 4/1996 | Tan et al. |
| 5,760,266 A | 6/1998 | Eaton et al. |
| 5,990,372 A | 11/1999 | Blankenship et al. |
| 6,049,011 A | 4/2000 | Kiss et al. |
| 6,190,623 B1 | 2/2001 | Sanger et al. |
| 6,210,791 B1 | 4/2001 | Skoog et al. |
| 6,278,033 B1 | 8/2001 | Flick et al. |
| 6,395,197 B1 | 5/2002 | Detering et al. |
| 6,442,931 B1 | 9/2002 | Vasin et al. |
| 6,443,354 B1 | 9/2002 | Plochl et al. |
| 6,465,701 B1 | 10/2002 | Marsella et al. |
| 6,478,535 B1 | 11/2002 | Chung et al. |
| 6,610,124 B1 | 8/2003 | Dolan et al. |
| 6,688,100 B2 | 2/2004 | Wherley et al. |
| 6,695,077 B2 | 2/2004 | Szymocha et al. |
| 6,761,777 B1 | 7/2004 | Radon |
| 6,764,602 B2 | 7/2004 | Shutt et al. |
| 6,821,500 B2 | 11/2004 | Fincke et al. |
| 6,953,567 B2 | 10/2005 | Griffiths |
| 6,953,867 B2 | 10/2005 | Cockman et al. |
| 6,962,199 B1 | 11/2005 | Tjeenk Willink |
| 7,000,306 B2 | 2/2006 | Rice et al. |
| 7,045,670 B2 | 5/2006 | Johnson et al. |
| 7,183,451 B2 | 2/2007 | Gattis et al. |
| 7,208,647 B2 | 4/2007 | Peterson et al. |
| 7,211,128 B2 | 5/2007 | Thomas et al. |
| 7,253,328 B2 | 8/2007 | Stauffer |
| 7,442,350 B1 | 10/2008 | Vanden Bussche |
| 7,655,135 B2 | 2/2010 | Havlik et al. |
| 7,667,085 B2 | 2/2010 | Gattis et al. |
| 7,692,051 B2 | 4/2010 | Johnson et al. |
| 7,744,763 B2 | 6/2010 | Cross et al. |
| 7,759,288 B2 | 7/2010 | Prichett et al. |
| 7,759,531 B2 | 7/2010 | Pinkos et al. |
| 7,763,163 B2 | 7/2010 | Koseoglu |
| 7,901,486 B2 | 3/2011 | Cross et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,919,431 B2 | 4/2011 | Johnson et al. |
| 8,013,196 B2 | 9/2011 | Mamedov et al. |
| 8,013,197 B2 | 9/2011 | Peterson et al. |
| 8,080,697 B2 | 12/2011 | Lin et al. |
| 8,088,962 B2 | 1/2012 | Klanner et al. |
| 8,137,476 B2 | 3/2012 | Morrow et al. |
| 8,211,312 B2 | 7/2012 | Stewart et al. |
| 2002/0154741 A1 | 10/2002 | Rigali et al. |
| 2004/0079228 A1 | 4/2004 | Wijmans et al. |
| 2005/0070748 A1 | 3/2005 | Ellis et al. |
| 2006/0283780 A1 | 12/2006 | Spivey et al. |
| 2007/0018038 A1 | 1/2007 | Jarmon et al. |
| 2007/0149807 A1 | 6/2007 | Dieterle et al. |
| 2007/0191664 A1 | 8/2007 | Hershkowitz et al. |
| 2009/0042998 A1 | 2/2009 | Hashimoto et al. |
| 2010/0005963 A1 | 1/2010 | Snape et al. |
| 2010/0044626 A1 | 2/2010 | Fischer et al. |
| 2010/0126909 A1 | 5/2010 | Bhasin et al. |
| 2010/0130803 A1 | 5/2010 | Keusenkothen et al. |
| 2010/0228069 A1 | 9/2010 | Kuznicki et al. |
| 2010/0319536 A1 | 12/2010 | Song et al. |
| 2011/0071331 A1 | 3/2011 | Basset et al. |
| 2011/0094378 A1 | 4/2011 | Mitariten |
| 2011/0114285 A1 | 5/2011 | Buxbaum |
| 2011/0297269 A1 | 12/2011 | Pilon et al. |
| 2012/0029256 A1 | 2/2012 | Chen et al. |
| 2012/0178833 A1 | 7/2012 | Clomburg, Jr. et al. |

FOREIGN PATENT DOCUMENTS

| | | |
|---|---|---|
| CN | 101928217 A | 12/2010 |
| CN | 201768561 U1 | 3/2011 |
| CN | 102247876 A | 11/2011 |
| DE | 3327000 A1 | 2/1985 |
| DE | 19626484 A1 | 1/1998 |
| DE | 10252859 A1 | 5/2004 |
| EA | 008761 B1 | 8/2007 |
| EA | 200800261 A1 | 4/2008 |
| EA | 013242 B1 | 4/2010 |
| EP | 0039918 A1 | 11/1981 |
| EP | 011707 B1 | 9/1982 |
| EP | 0158863 A2 | 10/1985 |
| EP | 0173501 A2 | 3/1986 |
| EP | 0263259 A2 | 4/1988 |
| EP | 1677910 A2 | 3/2005 |
| EP | 1667949 A2 | 4/2005 |
| EP | 1678274 A2 | 4/2005 |
| EP | 1856047 A2 | 8/2006 |
| EP | 2022772 A1 | 2/2009 |
| EP | 2224025 A1 | 9/2010 |
| EP | 2417721 A1 | 10/2010 |
| EP | 1663918 B1 | 2/2012 |
| EP | 2049456 B1 | 3/2012 |
| GB | 283163 A | 1/1929 |
| GB | 332258 A | 7/1930 |
| GB | 334193 A | 8/1930 |
| GB | 451794 A | 8/1936 |
| GB | 1358862 A | 7/1974 |
| GB | 2000180 A | 4/1979 |
| GB | 2220674 A | 1/1990 |
| JP | 6046976 A | 3/1985 |
| JP | 60129552 A | 7/1985 |
| JP | 1132535 A | 5/1989 |
| JP | 01277196 A | 11/1989 |
| JP | 2002348580 A | 12/2002 |
| KR | 2002009748 A | 2/2002 |
| RU | 1776652 A1 | 11/1992 |
| RU | 1778146 A1 | 11/1992 |
| RU | 2065866 C1 | 8/1996 |
| RU | 2145952 C1 | 2/2000 |
| RU | 98101950 A | 2/2000 |
| RU | 2158747 C1 | 11/2000 |
| RU | 2170617 C2 | 7/2001 |
| RU | 2187768 C2 | 8/2002 |
| RU | 2204434 C2 | 5/2003 |
| RU | 2222569 C2 | 1/2004 |
| RU | 2261995 C2 | 10/2005 |
| RU | 2264855 C2 | 11/2005 |
| RU | 2346737 C2 | 2/2009 |
| RU | 2363521 C1 | 8/2009 |
| RU | 2367668 C2 | 9/2009 |
| RU | 2373178 C2 | 11/2009 |
| RU | 2427608 C2 | 8/2011 |
| RU | 2438083 C2 | 12/2011 |
| RU | 2440962 C1 | 1/2012 |
| RU | 2443758 C2 | 2/2012 |
| RU | 116365 U1 | 5/2012 |
| RU | 2451658 C2 | 5/2012 |
| SU | 234422 A1 | 5/1969 |
| SU | 280739 A1 | 2/1976 |
| SU | 803969 A | 2/1981 |
| SU | 392723 A | 7/1983 |
| SU | 410596 A | 7/1983 |
| SU | 1613481 A1 | 12/1990 |
| WO | 9109829 A1 | 7/1991 |
| WO | 9518089 A1 | 7/1995 |
| WO | 9602792 A2 | 2/1996 |
| WO | 02058818 A2 | 8/2002 |
| WO | 03083015 A2 | 10/2003 |
| WO | 2004224220 A1 | 9/2004 |
| WO | 2009080621 A1 | 7/2009 |
| WO | 2009121456 A1 | 10/2009 |
| WO | 2010066281 A1 | 6/2010 |
| WO | 2010079177 A2 | 7/2010 |
| WO | 2010127752 A1 | 11/2010 |
| WO | 2011021024 A1 | 2/2011 |
| WO | 2011081836 A2 | 7/2011 |

(56) References Cited

FOREIGN PATENT DOCUMENTS

| | | |
|---|---|---|
| WO | 2011090616 A2 | 7/2011 |
| WO | 2012005862 A1 | 1/2012 |
| WO | 2012108686 A2 | 8/2012 |

OTHER PUBLICATIONS

Bartholome, "The BASF-process for production of acetylene by partial oxidation of gaseous hydrocarbons", Special Supplement to Chemical Engineering Science, 1954, pp. 94-104. vol. 3.
Bergeot, Simulated moving bed reactor for paraxylene production, Chemical Engineering Transactions, 2009, pp. 87-92, vol. 17.
Besev, "Radical Cyclization Approaches to Pyrrolidines", Acta Universitatis Upsaliensis, Uppsala University, 2002.
Biswas, "Enhanced production of 2,3-Butanediol by engineered *Bacillus subtilis*", Appl. Microbiol. Biotechnology, 2012, vol. 94, pp. 651-658.
Buhl, "Bio-Production of Light Olefins", ChemManager online, Europe, Mar. 19, 2012.
Cerff, "Supersonic Injection and Mixing in the Shock Wave Reactor", Thesis M.S. Aeronautics and Astronautics, University of Washington, 2010.
Chemsystems, "1,4-Butanediol/THF 98/99S1", Sep. 1999.
Chemsystems, "Acetylene Production Technologies Perp 05/06S9", Nexant, 2007.
Chemsystems, "Acrylic Acid Perp 08/09", Nexant, Aug. 2010.
Chemsystems, "Butadiene/Butylenes Perp 09/10-5", Nexant, Sep. 2010.
Chemsystems online, "Ethylene oxide/Ethylene Glycol", Nexant, 2009.
Chemsystems, "Green Propylene", Nexant, 2009.
Chemsystems, "Vinyl Chloride Monomer (VCM0/Ethylene Dichloride (EDC) Perp 08-09-4", Nexant, Oct. 2009.
Choudhury, "Thermal Decomposition of t-Butyl Alcohol in Shock Waves", Combustion Scienve and Technology, 1990, vol. 71, iss 4-6, pp. 219-232.
Collins, "Disproportionation of Toulene over ZSM-5 under Near-Critical Conditions", AlChe Journal, 1998, pp. 1211-1214, vol. 34, No. 7.
Fernandez, "A Noise-Temperature Measurement System Using a Cryogenic Attenuator", TMO Progress Report 42-135, 1998.
Garner, "Asymmetric Multicomponent [C+NC+CC] Synthesis of Highly Functionalized Pyrrolidines Catalyzed by Silver(I)", Organic Letters, 2006, pp. 3647-3650, vol. 8, No. 17.
Gorman, "Soluble, Highly Conjugated Derivatives of Polyacetylene from the Ring-Opening Metathesis Polymerization of Monosubstituted Cyclooctatetraenes: Synthesis and the Relationship between Polymer Structure and Physical Properties", Office of Naval Research, Technical Report 1, prepared for J. Am. Chem. Soc, 1993, vol. 115, pp. 1397-1409.
Hanika, "Catalytic Transalkylation of Trimethylbenzenes with Toulene", Petroleum and Coal, 2003. pages 78-82, vol. 45, 1-2.
Hendriksen, "Intermediates to Ethylene Glycol: Carbonylation of Formaldehyde Catalyzed by Nafion Solid Perfluorosulfonic Acid Resin", Exxon Research and Engineering Company, 1983.
Hoener, "The Production and Characterization of Mid-Gap States in trans-Polyacetylene", Thesis Ph.D, University of California, Berkeley, Aug. 1998.
Isis.com, "Caprolactam Production and Manufacturing Process", Chemical Report, Apr. 23, 2010.
Jui, "Enantioselective Organo-SOMO Cycloadditions: A Catalytic Approach to Complex Pyrrolidines from Olefins and Aldehydes", J. Am. Chem. So., 2012, pp. 11400-11403, vol. 134.
Kolts, "Enhanced Ethylene and Ethane Production with Free-Radical Cracking Catalysts", Science, May 1986, pp. 744-746, vol. 32.
Kopke, "2,3-Butanediol Production by Acetrogenic Bacteria, an Alternative Route to Chemical Synthesis, Using Industrial Waste Gas", Applied and Environmental Microbiology, 2011, pp. 5467-5475, vol. 77, No. 15.
Lim, "Production of Ethylbenzene from Benzene and Ethylene by Liquid-phase Alkylation Using Zeolite Catalysts", SRI Consulting, PEP Process Module, Oct. 1999.
Marcu, "Oxidative dehydrogenation of isobutane over a titanium pyrophosphate catalyst", J. Serb. Chem. Soc., 2005, pp. 791-798, vol. 70, 6.
Biochemistry Forum, "Three kinds of methyl acrylate production methods", Nature Network, Feb. 21, 2011.
Rep, "Side chain alkylation of toluene with methanol over basic zeolites—novel production route towards styrene?", Thesis—University of Twente, 2002.
Tai, "Temperature-controlled phase-transfer catalysis for ethylene glycol production from cellulose", Chem. Commun., 2012, pp. 7052-7054, vol. 48.
Takemoto, "Synthesis of Styrenes through the Biocatalytic Decarboxylation of trans-Cinnamic Acids by Plant Cell Cultures", Chem. Pharm. Bull., 2001, pp. 639-641, vol. 49, 5.
Tallman, "Naptha cracking for light olefins production", PTQ, 2010 Q3, pp. 87-91.
Towfighi, "Steam Cracking of Naptha in Packed Bed Reactors", Ind. Eng. Chem. Res., 2002, pp. 1419-1424, vol. 41.
Wang, "Review of Directly Producing Light Olefins via CO Hydrogenation", Journal of Natural Gas Chemistry, 2003, pp. 10-16, vol. 12.
White, "Novel Multistep Process for Production on N-Methyl-2-Pyrrolidone from Renewable Resources", Pacific Northwest National Laboratory, 2005.
Zimmermann, "Ethylene", Ullmann's Encyclopedia of Industrial Chemistry, Jun. 2000.
Zuidhof, "The Beckmann rearrangement of cyclohexanone oxime to ☐-caprolactam in micromixers and microchannels", Technische Universiteit Eindhoven, 2010.
U.S. Appl. No. 13/947,485, filed Jul. 22, 2013, Negiz et al.
U.S. Appl. No. 13/947,404, filed Jul. 22, 2013, Stevens et al.
U.S. Appl. No. 13/950,763, filed Jul. 25, 2013, Rende et al.
U.S. Appl. No. 13/925,115, filed Jun. 24, 2013, Rende et al.
U.S. Appl. No. 13/950,526, filed Jul. 25, 2013, Rende et al.
U.S. Appl. No. 13/941,631, filed Jul. 15, 2013, Rende et al.
U.S. Appl. No. 13/950,921, filed Jul. 25, 2013, Rende et al.
U.S. Appl. No. 13/950,886, filed Jul. 25, 2013, Rende et al.
U.S. Appl. No. 13/950,504, filed Jul. 25, 2013, Rende et al.
U.S. Appl. No. 13/950,475, filed Jul. 25, 2013, Rende et al.
U.S. Appl. No. 13/941,620, filed Jul. 15, 2013, Rende et al.
U.S. Appl. No. 13/942,676, filed Jul. 15, 2013, Rende et al.
U.S. Appl. No. 13/943,848, filed Jul. 17, 2013, Rende et al.
U.S. Appl. No. 13/943,845, filed Jul. 17, 2013, Rende et al.
U.S. Appl. No. 13/943,840, filed Jul. 17, 2013, Rende et al.
U.S. Appl. No. 13/942,871, filed Jul. 16, 2013, Rende et al.
U.S. Appl. No. 13/943,852, filed Jul. 17, 2013, Rende et al.
U.S. Appl. No. 13/942,682, filed Jul. 15, 2013, Rende et al.
U.S. Appl. No. 13/950,830, filed Jul. 25, 2013, Rende et al.
U.S. Appl. No. 13/943,856, filed Jul. 17, 2013, Rende et al.
U.S. Appl. No. 13/950,787, filed Jul. 25, 2013, Rende et al.
U.S. Appl. No. 13/966,367, filed Aug. 14, 2013, Bricker et al.
U.S. Appl. No. 13/915,143, filed Jun. 11, 2013, Bricker et al.
U.S. Appl. No. 13/915,151, filed Jun. 11, 2013, Bricker et al.
U.S. Appl. No. 13/915,020, filed Jun. 11, 2013, Bricker et al.
U.S. Appl. No. 13/915,159, filed Jun. 11, 2013, Bricker et al.
U.S. Appl. No. 13/915,057, filed Jun. 11, 2013, Bricker et al.
U.S. Appl. No. 13/915,099, filed Jun. 11, 2013, Bricker et al.
U.S. Appl. No. 13/915,106, filed Jun. 11, 2013, Bricker et al.
U.S. Appl. No. 13/915,113, filed Jun. 11, 2013, Bricker et al.
U.S. Appl. No. 13/915,130, filed Jun. 11, 2013, Bricker et al.
U.S. Appl. No. 13/966,544, filed Aug. 14, 2013, Bricker et al.
U.S. Appl. No. 13/967,459, filed Aug. 15, 2013, Rende et al.
U.S. Appl. No. 13/952,810, filed Jul. 29, 2013, Rende et al.
U.S. Appl. No. 13/916,913, filed Jun. 13, 2013, Bedard et al.
U.S. Appl. No. 13/967,327, filed Aug. 14, 2013, Bedard et al.
U.S. Appl. No. 13/966,961, filed Aug. 14, 2013, Bedard et al.
U.S. Appl. No. 13/966,752, filed Aug. 14, 2013, Bedard et al.
U.S. Appl. No. 13/964,458, filed Aug. 12, 2013, Bedard et al.
U.S. Appl. No. 13/964,486, filed Aug. 12, 2013, Bedard et al.
U.S. Appl. No. 13/964,396, filed Aug. 12, 2013, Bedard et al.

(56) References Cited

OTHER PUBLICATIONS

U.S. Appl. No. 13/964,498, filed Aug. 12, 2013, Bedard et al.
U.S. Appl. No. 13/916,924, filed Jun. 13, 2013, Bedard et al.
U.S. Appl. No. 13/916,936, filed Jun. 13, 2013, Bedard et al.
U.S. Appl. No. 13/967,373, filed Aug. 15, 2013, Bedard et al.
U.S. Appl. No. 13/967,334, filed Aug. 14, 2013, Bedard et al.
U.S. Appl. No. 13/967,404, filed Aug. 15, 2013, Bedard et al.
U.S. Appl. No. 13/967,397, filed Aug. 15, 2013, Bedard et al.
U.S. Appl. No. 13/967,391, filed Aug. 15, 2013, Bedard et al.
U.S. Appl. No. 13/967,428, filed Aug. 15, 2013, Bedard et al.
U.S. Appl. No. 13/967,440, filed Aug. 15, 2013, Bedard et al.
U.S. Appl. No. 13/967,533, filed Aug. 15, 2013, Bedard et al.
U.S. Appl. No. 13/967,674, filed Aug. 15, 2013, Bedard et al.
U.S. Appl. No. 13/964,524, filed Aug. 12, 2013, Bedard et al.
U.S. Appl. No. 13/967,697, filed Aug. 15, 2013, Bedard et al.
U.S. Appl. No. 13/967,792, filed Aug. 15, 2013, Bedard et al.
U.S. Appl. No. 13/964,411, filed Aug. 12, 2013, Towler et al.
U.S. Appl. No. 13/964,425, filed Aug. 12, 2013, Towler et al.
U.S. Appl. No. 13/916,966, filed Jun. 13, 2013, Bedard et al.
U.S. Appl. No. 13/967,741, filed Aug. 15, 2013, Towler et al.
Smidt et al., "The Oxidation of Olefins with Palladium Chloride Catalysts", Angew. Chem. Internatio. Edit., 1962, pp. 80-88, vol. 1, No. 2.
U.S. Appl. No. 13/947,519, filed Jul. 22, 2013, Negiz et al.
Beskov, "Chemical Technology and the Fundamentals of Industrial Ecology: Textbook for Universities", Moscow, Khimiya, 1999, p. 182-184.
Fischer, "Self-repairing material systems—a dream or a reality?", Natural Science, vol. 2, No. 8, 873-901 (2010).
Froggatt, "Nuclear Power: Myth and Reality", Dec. 2005, No. 2, Russian version, p. 24.
Knunyantsa, "Soviet Encyclopedia", G.A. Jagodin Publishing, Moscow, 1988, vol. 1, col. 209.
Knunyantsa, "Soviet Encyclopedia", G.A. Jagodin Publishing, Moscow, 1990, vol. 2, col. 249-250.
Knunyantsa, "Great Russian Encyclopedia", Scientific Publishing, Moscow, 1992, vol. 3, col. 649-650.
Knunyantsa "Soviet Encyclopedia", G.A. Jagodin Publishing, Moscow, 1988, vol. 1, col. 931.
Lefevr, "Processes in Combustion Chambers", MIR, Moscow, 1986, p. 317-323.
Matar, "Chemistry of Petrochemical Processes" Second Edition, Provides Quick and Easy Access to Hundreds of Reactions, Processes and Products, 1994, 2000 by Gulf Publishing Company, Houston, Texas, p. 392, p. 214, last paragraph, p. 95, p. 94, Figs. 3-12, p. 246-248, p. 206, lines 8-11, p. 209-210, p. 247, paragraph 1, p. 205-206, p. 33-34, p. 91, paragraph 1.
Nikitin, book "Brief Guidelines of Gas Welder and Burner", 1960, p. 24.
Novoselov, "Electric Field Effect in Atomically Thin Carbon Films", Science 306, 666-669 (2004).
Reed, "The Superalloys: Fundamentals and Applications", Cambridge University Press, 2006, p. 1.
Shah, Ullmann's Encyclopedia of Industrial Chemistry, 2007, Heat Exchange, p. 14-17, 27, 31, 46-48.
Zolotova, "Great Russian Encyclopedia", Scientific Publishing, Moscow, 1992, vol. 3, col. 5-8.
Laukhuf, "Adsorption of Carbon Dioxide, Acetylene, Ethane, and Propylene on Charcoal at Near Room Temperatures", Journal of Chemical and Engineering Data, vol. 14, No. 1, Jan. 1969, p. 48-51.
Ren, "Olefins from conventional and heavy feedstocks: Energy use in steam cracking and alternative processes", Energy 31 (2006) 425-451.
Search Report dated Dec. 12, 2013 for corresponding PCT Appl. No. PCT/US2013/053698.

\* cited by examiner

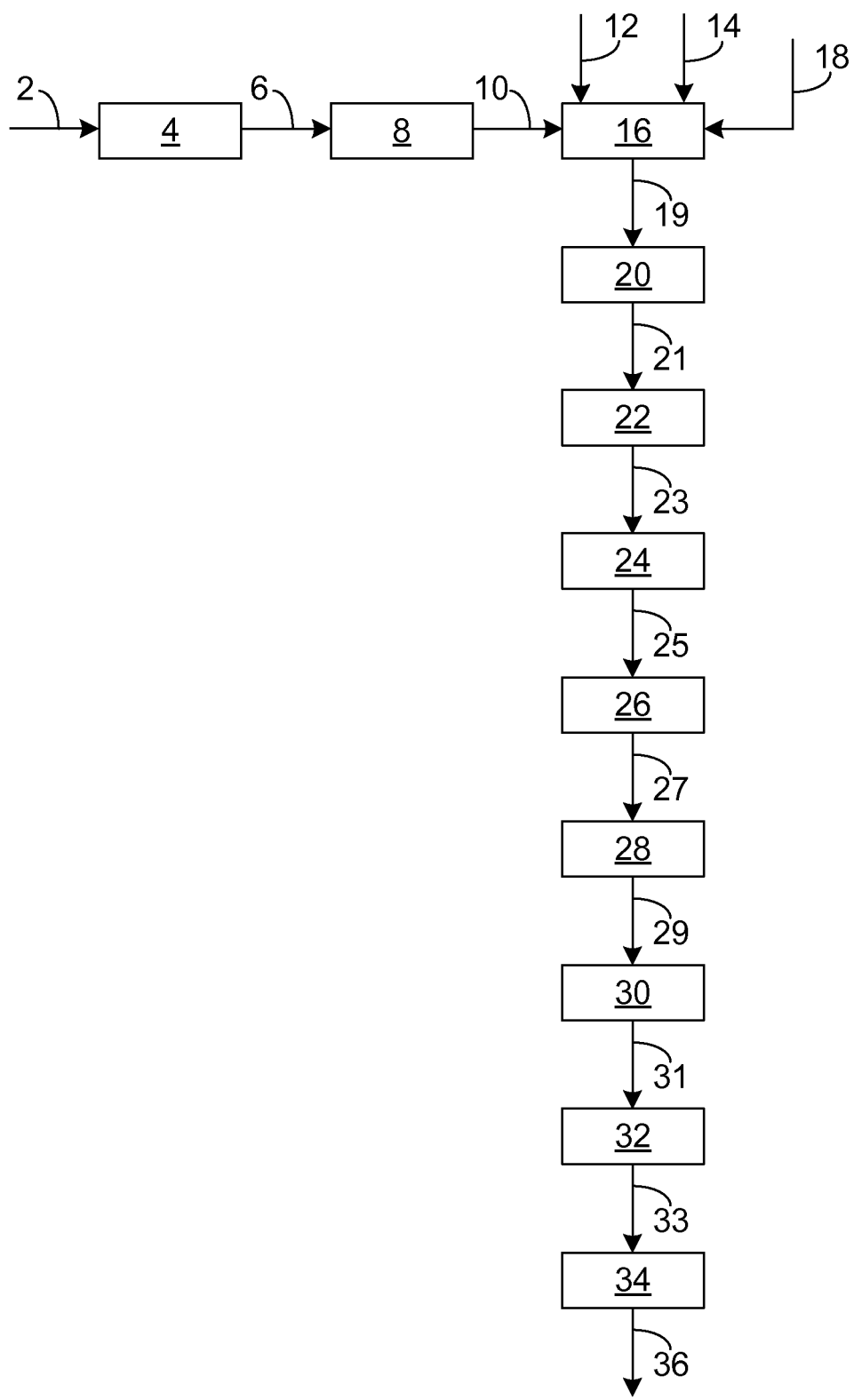

ACIDS REMOVAL AND METHANE CONVERSION PROCESS USING A SUPERSONIC FLOW REACTOR

CROSS-REFERENCE TO RELATED APPLICATION

This application claims priority from Provisional Application No. 61/691,355 filed Aug. 21, 2012, the contents of which are hereby incorporated by reference.

BACKGROUND OF THE INVENTION

A process is disclosed for removing contaminants from a process stream and converting methane in the process stream to acetylene using a supersonic flow reactor. More particularly, a process is provided for removal of trace and greater amounts of acids. This process can be used in conjunction with other contaminant removal processes including mercury removal, water and carbon dioxide removal, and removal of sulfur containing compounds containing these impurities from the process stream.

Light olefin materials, including ethylene and propylene, represent a large portion of the worldwide demand in the petrochemical industry. Light olefins are used in the production of numerous chemical products via polymerization, oligomerization, alkylation and other well-known chemical reactions. Producing large quantities of light olefin material in an economical manner, therefore, is a focus in the petrochemical industry. These light olefins are essential building blocks for the modern petrochemical and chemical industries. The main source for these materials in present day refining is the steam cracking of petroleum feeds.

The cracking of hydrocarbons brought about by heating a feedstock material in a furnace has long been used to produce useful products, including for example, olefin products. For example, ethylene, which is among the more important products in the chemical industry, can be produced by the pyrolysis of feedstocks ranging from light paraffins, such as ethane and propane, to heavier fractions such as naphtha. Typically, the lighter feedstocks produce higher ethylene yields (50-55% for ethane compared to 25-30% for naphtha); however, the cost of the feedstock is more likely to determine which is used. Historically, naphtha cracking has provided the largest source of ethylene, followed by ethane and propane pyrolysis, cracking, or dehydrogenation. Due to the large demand for ethylene and other light olefinic materials, however, the cost of these traditional feeds has steadily increased.

Energy consumption is another cost factor impacting the pyrolytic production of chemical products from various feedstocks. Over the past several decades, there have been significant improvements in the efficiency of the pyrolysis process that have reduced the costs of production. In a typical or conventional pyrolysis plant, a feedstock passes through a plurality of heat exchanger tubes where it is heated externally to a pyrolysis temperature by the combustion products of fuel oil or natural gas and air. One of the more important steps taken to minimize production costs has been the reduction of the residence time for a feedstock in the heat exchanger tubes of a pyrolysis furnace. Reduction of the residence time increases the yield of the desired product while reducing the production of heavier by-products that tend to foul the pyrolysis tube walls. However, there is little room left to improve the residence times or overall energy consumption in traditional pyrolysis processes.

More recent attempts to decrease light olefin production costs include utilizing alternative processes and/or feed streams. In one approach, hydrocarbon oxygenates and more specifically methanol or dimethylether (DME) are used as an alternative feedstock for producing light olefin products. Oxygenates can be produced from available materials such as coal, natural gas, recycled plastics, various carbon waste streams from industry and various products and by-products from the agricultural industry. Making methanol and other oxygenates from these types of raw materials is well established and typically includes one or more generally known processes such as the manufacture of synthesis gas using a nickel or cobalt catalyst in a steam reforming step followed by a methanol synthesis step at relatively high pressure using a copper-based catalyst.

Once the oxygenates are formed, the process includes catalytically converting the oxygenates, such as methanol, into the desired light olefin products in an oxygenate to olefin (OTO) process. Techniques for converting oxygenates, such as methanol to light olefins (MTO), are described in U.S. Pat. No. 4,387,263, which discloses a process that utilizes a catalytic conversion zone containing a zeolitic type catalyst. U.S. Pat. No. 4,587,373 discloses using a zeolitic catalyst like ZSM-5 for purposes of making light olefins. U.S. Pat. Nos. 5,095,163, 5,126,308 and 5,191,141 on the other hand, disclose an MTO conversion technology utilizing a non-zeolitic molecular sieve catalytic material, such as a metal aluminophosphate (ELAPO) molecular sieve. OTO and MTO processes, while useful, utilize an indirect process for forming a desired hydrocarbon product by first converting a feed to an oxygenate and subsequently converting the oxygenate to the hydrocarbon product. This indirect route of production is often associated with energy and cost penalties, often reducing the advantage gained by using a less expensive feed material.

Recently, attempts have been made to use pyrolysis to convert natural gas to ethylene. U.S. Pat. No. 7,183,451 discloses heating natural gas to a temperature at which a fraction is converted to hydrogen and a hydrocarbon product such as acetylene or ethylene. The product stream is then quenched to stop further reaction and subsequently reacted in the presence of a catalyst to form liquids to be transported. The liquids ultimately produced include naphtha, gasoline, or diesel. While this method may be effective for converting a portion of natural gas to acetylene or ethylene, it is estimated that this approach will provide only about a 40% yield of acetylene from a methane feed stream. While it has been identified that higher temperatures in conjunction with short residence times can increase the yield, technical limitations prevent further improvement to this process in this regard.

While the foregoing traditional pyrolysis systems provide solutions for converting ethane and propane into other useful hydrocarbon products, they have proven either ineffective or uneconomical for converting methane into these other products, such as, for example ethylene. While MTO technology is promising, these processes can be expensive due to the indirect approach of forming the desired product. Due to continued increases in the price of feeds for traditional processes, such as ethane and naphtha, and the abundant supply and corresponding low cost of natural gas and other methane sources available, for example the more recent accessibility of shale gas, it is desirable to provide commercially feasible and cost effective ways to use methane as a feed for producing ethylene and other useful hydrocarbons.

In the process of the present invention, it has been found important to minimize the concentration of water as well as carbon monoxide and carbon dioxide to avoid the occurrence of a water shift reaction which may result in undesired products being produced as well as reduce the quantity of the desired acetylene. Other contaminants should be removed for environmental, production or other reasons including the repeatability of the process. Since variations in the hydrocarbon stream being processed in accordance with this invention may result in product variations, it is highly desired to have consistency in the hydrocarbon stream even when it is provided from different sources. Natural gas wells from different regions will produce natural gas of differing compositions with anywhere from a few percent carbon dioxide up to a majority of the volume being carbon dioxide and the contaminant removal system will need to be designed to deal with such different compositions.

It has been found that a variety of hydrocarbon containing acids need to be removed from hydrocarbon streams. These include hydrochloric acid, sulfuric acid, hydrofluoric acid and organic acids, such as acetic acid, naphthenic acid, and other carboxylic acids and formic acid.

SUMMARY OF THE INVENTION

According to one aspect of the invention is provided a method for producing acetylene. The method generally includes introducing a feed stream portion of a hydrocarbon stream including methane into a supersonic reactor. The method also includes pyrolyzing the methane in the supersonic reactor to form a reactor effluent stream portion of the hydrocarbon stream including acetylene. The method further includes treating at least a portion of the hydrocarbon stream in a contaminant removal zone to remove acids such as hydrochloric acid, sulfuric acid, hydrofluoric acid and organic acids, such as acetic acid, naphthenic acid, and other carboxylic acids and formic acid from the process stream.

According to another aspect of the invention a method for controlling contaminant levels in a hydrocarbon stream in the production of acetylene from a methane feed stream is provided. The method includes introducing a feed stream portion of a hydrocarbon stream including methane into a supersonic reactor. The method also includes pyrolyzing the methane in the supersonic reactor to form a reactor effluent stream portion of the hydrocarbon stream including acetylene. The method further includes maintaining the concentration level of acids in at least a portion of the process stream to below specified levels.

According to yet another aspect of the invention is provided a system for producing acetylene from a methane feed stream. The system includes a supersonic reactor for receiving a methane feed stream and configured to convert at least a portion of methane in the methane feed stream to acetylene through pyrolysis and to emit an effluent stream including the acetylene. The system also includes a hydrocarbon conversion zone in communication with the supersonic reactor and configured to receive the effluent stream and convert at least a portion of the acetylene therein to another hydrocarbon compound in a product stream. The system includes a hydrocarbon stream line for transporting the methane feed stream, the reactor effluent stream, and the product stream. The system further includes a contaminant removal zone in communication with the hydrocarbon stream line for removing acids from the process stream from one or more of the methane feed stream, the effluent stream, and the product stream.

A single adsorbent layer to specifically remove the acids listed as contaminants here may be used. It is also contemplated that the invention would include the use of multi-layer adsorbent beds to remove other contaminants. The acids removal layer activated or promoted aluminas, silica gel, activated carbons or zeolites, such as 13X or 5A or other appropriate adsorbent. The water removal layer can be a variety of adsorbents, such as zeolite 3A, 4A, or 13X.

BRIEF DESCRIPTION OF THE DRAWING

The FIGURE shows the flow scheme for a process of producing a hydrocarbon product by use of a supersonic reactor with one or more contaminant removal zones employed in the process.

DETAILED DESCRIPTION

One proposed alternative to the previous methods of producing olefins that has not gained much commercial traction includes passing a hydrocarbon feedstock into a supersonic reactor and accelerating it to supersonic speed to provide kinetic energy that can be transformed into heat to enable an endothermic pyrolysis reaction to occur. Variations of this process are set out in U.S. Pat. Nos. 4,136,015 and 4,724,272, and SU 392723A. These processes include combusting a feedstock or carrier fluid in an oxygen-rich environment to increase the temperature of the feed and accelerate the feed to supersonic speeds. A shock wave is created within the reactor to initiate pyrolysis or cracking of the feed.

More recently, U.S. Pat. Nos. 5,219,530 and 5,300,216 have suggested a similar process that utilizes a shock wave reactor to provide kinetic energy for initiating pyrolysis of natural gas to produce acetylene. More particularly, this process includes passing steam through a heater section to become superheated and accelerated to a nearly supersonic speed. The heated fluid is conveyed to a nozzle which acts to expand the carrier fluid to a supersonic speed and lower temperature. An ethane feedstock is passed through a compressor and heater and injected by nozzles to mix with the supersonic carrier fluid to turbulently mix together at a Mach 2.8 speed and a temperature of about 427° C. The temperature in the mixing section remains low enough to restrict premature pyrolysis. The shockwave reactor includes a pyrolysis section with a gradually increasing cross-sectional area where a standing shock wave is formed by back pressure in the reactor due to flow restriction at the outlet. The shock wave rapidly decreases the speed of the fluid, correspondingly rapidly increasing the temperature of the mixture by converting the kinetic energy into heat. This immediately initiates pyrolysis of the ethane feedstock to convert it to other products. A quench heat exchanger then receives the pyrolized mixture to quench the pyrolysis reaction.

Methods and systems for converting hydrocarbon components in methane feed streams using a supersonic reactor are generally disclosed. As used herein, the term "methane feed stream" includes any feed stream comprising methane. The methane feed streams provided for processing in the supersonic reactor generally include methane and form at least a portion of a process stream that includes at least one contaminant. The methods and systems presented herein remove or convert the contaminant in the process stream and convert at least a portion of the methane to a desired product hydrocarbon compound to produce a product stream having a reduced contaminant level and a higher concentration of the product hydrocarbon compound relative to the feed stream. By one approach, a hydrocarbon stream portion of the process stream includes the contaminant and methods and systems presented herein remove or convert the contaminant in the hydrocarbon stream.

The term "hydrocarbon stream" as used herein refers to one or more streams that provide at least a portion of the methane feed stream entering the supersonic reactor as described herein or are produced from the supersonic reactor from the methane feed stream, regardless of whether further treatment or processing is conducted on such hydrocarbon stream. The "hydrocarbon stream" may include the methane feed stream, a supersonic reactor effluent stream, a desired product stream exiting a downstream hydrocarbon conversion process or any intermediate or by-product streams formed during the processes described herein. The hydrocarbon stream may be carried via a process stream. The term "process stream" as used herein includes the "hydrocarbon stream" as described above, as well as it may include a carrier fluid stream, a fuel stream, an oxygen source stream, or any streams used in the systems and the processes described herein.

Prior attempts to convert light paraffin or alkane feed streams, including ethane and propane feed streams, to other hydrocarbons using supersonic flow reactors have shown promise in providing higher yields of desired products from a particular feed stream than other more traditional pyrolysis systems. Specifically, the ability of these types of processes to provide very high reaction temperatures with very short associated residence times offers significant improvement over traditional pyrolysis processes. It has more recently been realized that these processes may also be able to convert methane to acetylene and other useful hydrocarbons, whereas more traditional pyrolysis processes were incapable or inefficient for such conversions.

The majority of previous work with supersonic reactor systems, however, has been theoretical or research based, and thus has not addressed problems associated with practicing the process on a commercial scale. In addition, many of these prior disclosures do not contemplate using supersonic reactors to effectuate pyrolysis of a methane feed stream, and tend to focus primarily on the pyrolysis of ethane and propane. One problem that has recently been identified with adopting the use of a supersonic flow reactor for light alkane pyrolysis, and more specifically the pyrolysis of methane feeds to form acetylene and other useful products therefrom, includes negative effects that particular contaminants in commercial feed streams can create on these processes and/or the products produced therefrom. Previous work has not considered contaminants and the need to control or remove specific contaminants, especially in light of potential downstream processing of the reactor effluent stream.

The term "adsorption" as used herein encompasses the use of a solid support to remove atoms, ions or molecules from a gas or liquid. The adsorption may be by "physisorption" in which the adsorption involves surface attractions or "chemisorptions" where there are actual chemical changes in the contaminant that is being removed. Depending upon the particular adsorbent, contaminant and stream being purified, the adsorption process may be regenerative or nonregenerative. Either pressure swing adsorption, temperature swing adsorption or displacement processes may be employed in regenerative processes. A combination of these processes may also be used. The adsorbents may be any porous material known to have application as an adsorbent including carbon materials such as activated carbon clays, molecular sieves including zeolites and metal organic frameworks (MOFs), metal oxides including silica gel and aluminas that are promoted or activated, as well as other porous materials that can be used to remove or separate contaminants.

"Pressure swing adsorption (PSA)" refers to a process where a contaminant is adsorbed from a gas when the process is under a relatively higher pressure and then the contaminant is removed or desorbed thus regenerating the adsorbent at a lower pressure.

"Temperature swing adsorption (TSA)" refers to a process where regeneration of the adsorbent is achieved by an increase in temperature such as by sending a heated gas through the adsorbent bed to remove or desorb the contaminant. Then the adsorbent bed is often cooled before resumption of the adsorption of the contaminant.

"Displacement" refers to a process where the regeneration of the adsorbent is achieved by desorbing the contaminant with another liquid that takes its place on the adsorbent. Such as process is shown in U.S. Pat. No. 8,211,312 in which a feed and a desorbent are applied at different locations along an adsorbent bed along with withdrawals of an extract and a raffinate. The adsorbent bed functions as a simulated moving bed. A circulating adsorbent chamber fluid can simulate a moving bed by changing the composition of the liquid surrounding the adsorbent. Changing the liquid can cause different chemical species to be adsorbed on, and desorbed from, the adsorbent. As an example, initially applying the feed to the adsorbent can result in the desired compound or extract to be adsorbed on the adsorbent, and subsequently applying the desorbent can result in the extract being desorbed and the desorbent being adsorbed. In such a manner, various materials may be extracted from a feed. In some embodiments of the present invention, a displacement process may be employed.

In accordance with various embodiments disclosed herein, therefore, processes and systems for removing or converting contaminants in methane feed streams are presented. The removal of particular contaminants and/or the conversion of contaminants into less deleterious compounds has been identified to improve the overall process for the pyrolysis of light alkane feeds, including methane feeds, to acetylene and other useful products. In some instances, removing these compounds from the hydrocarbon or process stream has been identified to improve the performance and functioning of the supersonic flow reactor and other equipment and processes within the system. Removing these contaminants from hydrocarbon or process streams has also been found to reduce poisoning of downstream catalysts and adsorbents used in the process to convert acetylene produced by the supersonic reactor into other useful hydrocarbons, for example hydrogenation catalysts that may be used to convert acetylene into ethylene. Still further, removing certain contaminants from a hydrocarbon or process stream as set forth herein may facilitate meeting product specifications.

In accordance with one approach, the processes and systems disclosed herein are used to treat a hydrocarbon process stream, to remove one or more contaminants therefrom and convert at least a portion of methane to acetylene. The hydrocarbon process stream described herein includes the methane feed stream provided to the system, which includes methane and may also include ethane or propane. The methane feed stream may also include combinations of methane, ethane, and propane at various concentrations and may also include other hydrocarbon compounds. In one approach, the hydrocarbon feed stream includes natural gas. The natural gas may be provided from a variety of sources including, but not limited to, gas fields, oil fields, coal fields, fracking of shale fields, biomass, and landfill gas. In another approach, the methane feed stream can include a stream from another portion of a refinery or processing plant. For example, light alkanes, including methane, are often separated during processing of crude oil into various products and a methane feed stream may be provided from one of these sources. These streams may be provided from the same refinery or different refinery or from a refinery off gas. The methane feed stream may include a stream from combinations of different sources as well.

In accordance with the processes and systems described herein, a methane feed stream may be provided from a remote location or at the location or locations of the systems and methods described herein. For example, while the methane feed stream source may be located at the same refinery or processing plant where the processes and systems are carried out, such as from production from another on-site hydrocarbon conversion process or a local natural gas field, the methane feed stream may be provided from a remote source via pipelines or other transportation methods. For example a feed stream may be provided from a remote hydrocarbon processing plant or refinery or a remote natural gas field, and provided as a feed to the systems and processes described herein. Initial processing of a methane stream may occur at the remote source to remove certain contaminants from the methane feed stream. Where such initial processing occurs, it may be considered part of the systems and processes described herein, or it may occur upstream of the systems and processes described herein. Thus, the methane feed stream provided for the systems and processes described herein may have varying levels of contaminants depending on whether initial processing occurs upstream thereof.

In one example, the methane feed stream has a methane content ranging from about 50 to about 100 mol-%. In another example, the concentration of methane in the hydrocarbon feed ranges from about 70 to about 100 mol-% of the hydrocarbon feed. In yet another example, the concentration of methane ranges from about 90 to about 100 mol-% of the hydrocarbon feed.

In one example, the concentration of ethane in the methane feed ranges from about 0 to about 30 mol-% and in another example from about 0 to about 10 mol-%. In one example, the concentration of propane in the methane feed ranges from about 0 to about 10 mol-% and in another example from about 0 to about 2 mol-%. The methane feed stream may also include heavy hydrocarbons, such as aromatics, paraffinic, olefinic, and naphthenic hydrocarbons. These heavy hydrocarbons if present will likely be present at concentrations of between about 0 mol-% and about 100 mol-%. In another example, they may be present at concentrations of between about 0 mol-% and 10 mol-% and may be present at between about 0 mol-% and 2 mol-%.

The present invention relates to the removal of acids from a hydrocarbon feedstock, preferably with activated or promoted aluminas, metal oxides or carbonates or type 13X zeolite if the contaminat is present in trace levels upto a few 100 ppm(v). At higher acid concentrations a basic solvent such as sodium hydroxide may be used. Certain zeolite/alumina hybrid adsorbents may also be used. The zeolites that can be used may include faujasites (13X, CaX, NaY, CaY, ZnX), chabazites, clinoptilolites and LTA (4A, 5A) zeolites. Other adsorbents may be used including silica gels and activated carbons.

In one embodiment, a water or a caustic wash may precede an acid removal adsorbent bed. This is applicable in situations where greater than trace levels of acids are to be removed. The water or caustic wash is employed to attain bulk removal while the adsorption bed is used for trace removal of the acids. The process includes a water wash of reactor effluent from quench zone in zone 20 (quench or wash tower). Zone 28 or 30 may also include an acid removal step as needed to remove acids formed in the hydrocarbon conversion zone. A neutralizing agent (i.e. caustic) may be added to water circulated to the wash tower.

At very low levels (<10 ppm (v)), the acids are not expected to adversely affect the supersonic reactor metallurgy or yields. However, at higher concentration, the combined effect of steam and acids may result in corrosion of the reactor metallurgy. In this case, an acid removal process needs to be implemented upstream of the supersonic reactor. The presence of polar compounds, water and dissociated oxygen in the reactor is likely to lead to the formation of some acids in the pyrolysis reactor. These acids need be removed downstream of the supersonic reactor to eliminate potential for fouling and corrosion in downstream processes and heat exchangers. Whether it is advantageous to have a single or two different acid removal systems (upstream and downstream) depends on the economics of corrosion/fouling versus cost of removal.

In one embodiment, the hydrocarbon feedstock is purified by passage through a multi-layer bed for removal of more than one type of contaminant.

Another type of adsorbent layer for acid removal that is effective in the practice of the present invention is an activated or promoted alumina. The promoter is selected from one or more alkali metals or alkaline earth metals. The preferred alkali metals include sodium and potassium and the preferred alkaline earth metals include magnesium and calcium.

By one aspect, the hydrocarbon stream includes one or more contaminants including or more type of acids and compounds containing acids. While the systems and processes are described generally herein with regard to removing these contaminants from a hydrocarbon stream, it should be understood that these contaminants may also be removed from other portions of the process stream.

According to one aspect, the contaminants in the hydrocarbon stream may be naturally occurring in the feed stream, such as, for example, present in a natural gas source or added to the feed stream in the process of extracting the natural gas. According to another aspect, the contaminants may be added to the hydrocarbon stream during a particular process step. In accordance with another aspect, the contaminant may be formed as a result of a specific step in the process, such as a product or by-product of a particular reaction, such as oxygen or carbon dioxide reacting with a hydrocarbon to form an oxygenate.

The process for forming acetylene from the methane feed stream described herein utilizes a supersonic flow reactor for pyrolyzing methane in the feed stream to form acetylene. The supersonic flow reactor may include one or more reactors capable of creating a supersonic flow of a carrier fluid and the methane feed stream and expanding the carrier fluid to initiate the pyrolysis reaction. In one approach, the process may include a supersonic reactor as generally described in U.S. Pat. No. 4,724,272, which is incorporated herein by reference, in their entirety. In another approach, the process and system may include a supersonic reactor such as described as a "shock wave" reactor in U.S. Pat. Nos. 5,219,530 and 5,300, 216, which are incorporated herein by reference, in their entirety. In yet another approach, the supersonic reactor described as a "shock wave" reactor may include a reactor such as described in "Supersonic Injection and Mixing in the Shock Wave Reactor" Robert G. Cerff, University of Washington Graduate School, 2010.

In an embodiment of the invention, the feed stream 2 is heated prior to being injected into the supersonic reactor. Depending upon the design of the supersonic reactor, the methane feed stream may be heated to a temperature greater than about 200° C. The methane feed stream may be heated to a temperature between about 200 to 1500° C. or between 500 to 1000° C.

While a variety of supersonic reactors may be used in the present process, an exemplary reactor will have a supersonic reactor that includes a reactor vessel generally defining a reactor chamber. While the reactor will often be found as a single reactor, it should be understood that it may be formed modularly or as separate vessels. A combustion zone or chamber is provided for combusting a fuel to produce a carrier fluid with the desired temperature and flowrate. The reactor may optionally include a carrier fluid inlet for introducing a supplemental carrier fluid into the reactor. One or more fuel injectors are provided for injecting a combustible fuel, for example hydrogen, into the combustion chamber. The same or other injectors may be provided for injecting an oxygen source into the combustion chamber to facilitate combustion of the fuel. The fuel and oxygen are combusted to produce a hot carrier fluid stream typically having a temperature of from about 1200° to about 3500° C. in one example, between about 2000° and about 3500° C. in another example, and between about 2500° and 3200° C. in yet another example. According to one example the carrier fluid stream has a pressure of about 1 atm or higher, greater than about 2 atm in another example, and greater than about 4 atm in another example.

The hot carrier fluid stream from the combustion zone is passed through a converging-diverging nozzle to accelerate the flowrate of the carrier fluid to above about Mach 1.0 in one example, between about Mach 1.0 and Mach 4.0 in another example, and between about Mach 1.5 and Mach 3.5 in another example. In this regard, the residence time of the fluid in the reactor portion of the supersonic flow reactor is between about 0.5 and 100 ms in one example, about 1.0 and 50 ms in another example, and about 1.5 and 20 ms in another example.

A feedstock inlet is provided for injecting the methane feed stream into the reactor to mix with the carrier fluid. The feedstock inlet may include one or more injectors for injecting the feedstock into the nozzle, a mixing zone, an expansion zone, or a reaction zone or a chamber. The injector may include a manifold, including for example a plurality of injection ports.

In one approach, the reactor may include a mixing zone for mixing of the carrier fluid and the feed stream. In another approach, no mixing zone is provided, and mixing may occur in the nozzle, expansion zone, or reaction zone of the reactor. An expansion zone includes a diverging wall to produce a rapid reduction in the velocity of the gases flowing therethrough, to convert the kinetic energy of the flowing fluid to thermal energy to further heat the stream to cause pyrolysis of the methane in the feed, which may occur in the expansion section and/or a downstream reaction section of the reactor. The fluid is quickly quenched in a quench zone to stop the pyrolysis reaction from further conversion of the desired acetylene product to other compounds. Spray bars may be used to introduce a quenching fluid, for example water or steam into the quench zone.

The reactor effluent exits the reactor via the outlet and as mentioned above forms a portion of the hydrocarbon stream. The effluent will include a larger concentration of acetylene than the feed stream and a reduced concentration of methane relative to the feed stream. The reactor effluent stream may also be referred to herein as an acetylene stream as it includes an increased concentration of acetylene. The acetylene may be an intermediate stream in a process to form another hydrocarbon product or it may be further processed and captured as an acetylene product stream. In one example, the reactor effluent stream has an acetylene concentration prior to the addition of quenching fluid ranging from about 4 to about 60 mol-%. In another example, the concentration of acetylene ranges from about 10 to about 50 mol-% and from about 15 to about 47 mol-% in another example.

In one example, the reactor effluent stream has a reduced methane content relative to the methane feed stream ranging from about 10 to about 90 mol-%. In another example, the concentration of methane ranges from about 30 to about 85 mol-% and from about 40 to about 80 mol-% in another example.

In one example the yield of acetylene produced from methane in the feed in the supersonic reactor is between about 40 and about 95 mol-%. In another example, the yield of acetylene produced from methane in the feed stream is between about 50 and about 90 mol-%. Advantageously, this provides a better yield than the estimated 40% yield achieved from previous, more traditional, pyrolysis approaches.

By one approach, the reactor effluent stream is reacted to form another hydrocarbon compound. In this regard, the reactor effluent portion of the hydrocarbon stream may be passed from the reactor outlet to a downstream hydrocarbon conversion process for further processing of the stream. While it should be understood that the reactor effluent stream may undergo several intermediate process steps, such as, for example, water removal, adsorption, and/or absorption to provide a concentrated acetylene stream, these intermediate steps will not be described in detail herein except where particularly relevant to the present invention.

The reactor effluent stream having a higher concentration of acetylene may be passed to a downstream hydrocarbon conversion zone where the acetylene may be converted to form another hydrocarbon product. The hydrocarbon conversion zone may include a hydrocarbon conversion reactor for converting the acetylene to another hydrocarbon product. While in one embodiment the invention involves a process for converting at least a portion of the acetylene in the effluent stream to ethylene through hydrogenation in a hydrogenation reactor, it should be understood that the hydrocarbon conversion zone may include a variety of other hydrocarbon conversion processes instead of or in addition to a hydrogenation reactor, or a combination of hydrocarbon conversion processes. Similarly the process and equipment as discussed herein may be modified or removed and not intended to be limiting of the processes and systems described herein. Specifically, it has been identified that several other hydrocarbon conversion processes, other than those disclosed in previous approaches, may be positioned downstream of the supersonic reactor, including processes to convert the acetylene into other hydrocarbons, including, but not limited to: alkenes, alkanes, methane, acrolein, acrylic acid, acrylates, acrylamide, aldehydes, polyacetylides, benzene, toluene, styrene, aniline, cyclohexanone, caprolactam, propylene, butadiene, butyne diol, butandiol, $C_2$-$C_4$ hydrocarbon compounds, ethylene glycol, diesel fuel, diacids, diols, pyrrolidines, and pyrrolidones.

A contaminant removal zone for removing one or more contaminants from the hydrocarbon or process stream may be located at various positions along the hydrocarbon or process stream depending on the impact of the particular contaminant on the product or process and the reason for the contaminants removal, as described further below. For example, particular contaminants have been identified to interfere with the operation of the supersonic flow reactor and/or to foul components in the supersonic flow reactor. Thus, according to one approach, a contaminant removal zone is positioned upstream of the supersonic flow reactor in order to remove these contaminants from the methane feed stream prior to introducing the stream into the supersonic reactor. Other contaminants have been identified to interfere with a downstream processing step or hydrocarbon conversion process, in which case the contaminant removal zone may be positioned upstream of the supersonic reactor or between the supersonic reactor and the particular downstream processing step at issue. Still other contaminants have been identified that should be removed to meet particular product specifications. Where it is desired to remove multiple contaminants from the hydrocarbon or process stream, various contaminant removal zones may be positioned at different locations along the hydrocarbon or process stream. In still other approaches, a contaminant removal zone may overlap or be integrated with another process within the system, in which case the contaminant may be removed during another portion of the process, including, but not limited to the supersonic reactor or the downstream hydrocarbon conversion zone. This may be accomplished with or without modification to these particular zones, reactors or processes. While the contaminant removal zone is often positioned downstream of the hydrocarbon conversion reactor, it should be understood that the contaminant removal zone in accordance herewith may be positioned upstream of the supersonic flow reactor, between the supersonic flow reactor and the hydrocarbon conversion zone, or downstream of the hydrocarbon conversion zone or along other streams within the process stream, such as, for example, a carrier fluid stream, a fuel stream, an oxygen source stream, or any streams used in the systems and the processes described herein.

In one approach, a method includes removing a portion of contaminants from the hydrocarbon stream. In this regard, the hydrocarbon stream may be passed to the contaminant removal zone. In one approach, the method includes controlling the contaminant concentration in the hydrocarbon stream. The contaminant concentration may be controlled by maintaining the concentration of contaminant in the hydrocarbon stream to below a level that is tolerable to the supersonic reactor or a downstream hydrocarbon conversion process. In one approach, the contaminant concentration is controlled by removing at least a portion of the contaminant from the hydrocarbon stream. As used herein, the term removing may refer to actual removal, for example by adsorption, absorption, or membrane separation, or it may refer to conversion of the contaminant to a more tolerable compound, or both. In one example, the contaminant concentration is controlled to maintain the level of contaminant in the hydrocarbon stream to below a harmful level. In another example, the contaminant concentration is controlled to maintain the level of contaminant in the hydrocarbon stream to below a lower level. In yet another example, the contaminant concentration is controlled to maintain the level of contaminant in the hydrocarbon stream to below an even lower level.

The FIGURE provides a flow scheme for an embodiment of the invention. In the FIGURE, a hydrocarbon feed 2, such as methane, is shown entering a first contaminant removal zone 4, then passing through line 6 to one or more heaters 8. A heated hydrocarbon feed 10 then enters a supersonic reactor 16 together with fuel 12, oxidizer 14 and optional steam 18. In the supersonic reactor, a product stream containing acetylene is produced. The product stream 19 from supersonic reactor 16 may then go to a second contaminant removal zone 20, through line 21 to a compression and adsorption/separation zone 22. If further purification is necessary, the stream passes through line 23 into a third contaminant removal zone 24. A purified acetylene stream 25 is sent to hydrocarbon conversion zone 26 to be converted into one or more hydrocarbon products which contain one or more impurities. These one or more hydrocarbon products 27 are shown being sent to a separation zone 28, then through line 29 to fourth contaminant removal zone 30, then through line 31 to a polishing reactor 32 to convert unreacted acetylene to the one or more hydrocarbon products. The now purified product stream 33 is sent to a product separation zone 34 and the primary product stream 36 is shown exiting at the bottom. Secondary products may also be produced. While there is a single contaminant removal zone shown in four locations in the FIGURE, each single contaminant removal zone may comprise one or more separate beds or other contaminant removal apparatus. In some embodiments of the invention, there may be fewer contaminant removal zones depending upon the quality of the hydrocarbon feed 2, product stream 19 and primary product stream 36.

While there have been illustrated and described particular embodiments and aspects, it will be appreciated that numerous changes and modifications will occur to those skilled in the art, and it is intended in the appended claims to cover all those changes and modifications which fall within the true spirit and scope of the present disclosure and appended claims.

The invention claimed is:

1. A method for producing acetylene comprising:
introducing a feed stream portion of a hydrocarbon stream comprising methane into a supersonic reactor;
pyrolyzing the methane in the supersonic reactor to form a reactor effluent stream portion of the hydrocarbon stream comprising acetylene; and
treating at least a portion of the hydrocarbon stream in a contaminant removal zone to remove acids from the hydrocarbon stream wherein said contaminant removal zone comprises an adsorbent bed wherein said hydrocarbon stream is contacted with an adsorbent material comprising one or more adsorbents to remove said acids, wherein one or more additional acids are removed and at least one acid is selected from the group consisting of acetic acid, formic acid and naphthenic acid.

2. The method of claim 1 wherein said contaminant removal zone comprises water or a basic solution that contacts said hydrocarbon stream to remove said acids.

3. The method of claim 1 wherein pyrolyzing the methane includes accelerating the hydrocarbon stream to a velocity of between about Mach 1.0 and about Mach 4.0 to create a shockwave, thereby slowing down the hydrocarbon stream to increase the temperature of the hydrocarbon process stream.

4. The method of claim 1 wherein pyrolyzing the methane includes heating the methane to a temperature of between about 1200° and about 3500° C. for a residence time of between about 0.5 and about 100 ms.

5. The method of claim 1 further comprising treating said at least a portion of the hydrocarbon stream to remove other contaminants.

6. The method of claim 1 wherein said adsorbent is a zeolite is selected from the group consisting of faujasites (13X, CaX, NaY, CaY, and ZnX), chabazites, clinoptilolites and LTA (4A, 5A) zeolites.

7. The method of claim 1 wherein said adsorbent is a silica gel or an activated carbon.

8. The method of claim 1 wherein an additional acid is selected from the group consisting of hydrochloric acid, sulfuric acid and hydrofluoric acid.

9. The method of claim 2 wherein the basic solution is sodium hydroxide.

10. A method for producing acetylene comprising:
introducing a feed stream portion of a hydrocarbon stream comprising methane into a supersonic reactor;
pyrolyzing the methane in the supersonic reactor to form a reactor effluent stream portion of the hydrocarbon stream comprising acetylene; and treating at least a portion of the hydrocarbon stream in a contaminant removal zone to remove acids from the hydrocarbon stream wherein the contaminant removal zone is positioned upstream of the supersonic reactor to remove the portion of the acids from the hydrocarbon stream prior to introducing the process stream into the supersonic reactor.

11. The method of claim 1 wherein said adsorbent is an activated or promoted alumina wherein a promoter in said promoted alumina is an alkali metal or an alkali earth metal.

12. The method of claim 11 wherein said alkali metal is selected from the group consisting of lithium, sodium, potassium and said alkaline earth metals are selected from the group consisting of beryllium, magnesium and calcium.

* * * * *